(12) United States Patent
Liu et al.

(10) Patent No.: US 7,586,094 B2
(45) Date of Patent: Sep. 8, 2009

(54) BACKGROUND COMPENSATION BY MULTIPLE-PEAK MEASUREMENTS FOR ABSORPTION SPECTROSCOPY-BASED GAS SENSING

(75) Inventors: Xiang Liu, Phoenix, AZ (US); Xin Zhou, Rancho Cucamonga, CA (US); Alfred Feitisch, Los Gatos, CA (US); Gregory M. Sanger, Chico, CA (US)

(73) Assignee: Spectrasensors, Inc., Rancho Cucamonga, CA (US)

( * ) Notice: Subject to any disclaimer, the term of this patent is extended or adjusted under 35 U.S.C. 154(b) by 0 days.

(21) Appl. No.: 11/929,525

(22) Filed: Oct. 30, 2007

(65) Prior Publication Data

US 2008/0179530 A1    Jul. 31, 2008

Related U.S. Application Data

(60) Provisional application No. 60/898,475, filed on Jan. 30, 2007.

(51) Int. Cl.
*G01J 5/02*    (2006.01)
(52) U.S. Cl. ..................................... 250/343
(58) Field of Classification Search ............... 250/343, 250/344
See application file for complete search history.

(56) References Cited

U.S. PATENT DOCUMENTS

| | | | |
|---|---|---|---|
| 3,979,589 A | | 9/1976 | Sternberg et al. |
| 4,567,366 A | * | 1/1986 | Shinohara ............... 250/339.13 |
| 4,692,622 A | * | 9/1987 | Taniguchi et al. ............ 250/343 |
| 4,937,448 A | * | 6/1990 | Mantz et al. ................. 250/343 |
| 5,047,639 A | * | 9/1991 | Wong ....................... 250/341.1 |
| 5,124,553 A | * | 6/1992 | Hilliard et al. ............... 250/344 |
| 5,281,816 A | * | 1/1994 | Jacobson et al. ......... 250/339.05 |
| 5,559,333 A | * | 9/1996 | Araya et al. ................. 250/344 |
| 6,657,198 B1 | | 12/2003 | May |
| 7,132,661 B2 | | 11/2006 | May |
| 2006/0243931 A1 | * | 11/2006 | Haran et al. ................. 250/574 |

OTHER PUBLICATIONS

Zhou et al., "Development of a sensor for temperature and water concentration in combustion gases using a single tunable diode laser," 2003 Institute of Physics Publishing, Measurement Science and Technology, vol. 14, pp. 1459-1468.*

(Continued)

*Primary Examiner*—David P Porta
*Assistant Examiner*—Kiho Kim
(74) *Attorney, Agent, or Firm*—Mintz, Levin, Cohn, Ferris, Glovsky & Popeo, P.C.

(57) ABSTRACT

Concentrations of a target analyte in a gas mixture containing one or more background analytes having potentially interfering spectral absorption features can be calculated by compensating for background analyte absorption at a target wavelength used to quantify the target analyte. Absorption can be measured at a reference wavelength chosen to quantify the concentration of the background analyte. Using a background gas adjustment factor or function, the absorption measured at the reference wavelength can be used to calculate absorption due to the background analyte at the target wavelength and thereby compensate for this background absorption to more accurately calculate the target analyte concentration in real or near real time. Additional background analytes can optionally be compensated for by using one or more additional reference wavelengths.

27 Claims, 7 Drawing Sheets

OTHER PUBLICATIONS

Nagali et al., "Design of a diode-laser sensor to monitor water vapor in high-pressure combustion gases,", Dec. 1997, Applied Optics, vol. 36, No. 36, pp. 9518-9527.*

Tecihert et al., "Simultaneous in situ measurement of CO, H2O, and gas temperature in a full-sized coal-fired power plant by near-IR diode laser," Apr. 2003, Applied Optics, vol. 42, No. 12, pp. 2043-2051.*

Arroyo et al., "Diode-laser absorption technique for simultaneous measurements of mutiple gasdynamic parameters in high-speed flows containing water vapor,", May 1994, Applied Optics, vol. 33, No. 15, pp. 3296-3307.*

International Search Report for related patent PCT/US2008/051931 performed by International Searching Authority/EP on Oct. 17, 2008.

Written Opinion of the International Searching Authority for related patent PCT/US2008/051931 performed by International Searching Authority/EP on Oct. 17, 2008.

Edwards, C. S. et al. "A tunable diode laser absorption spectrometer for moisture measurements in the low parts in 109 range; a tunable diode laser absorption spectrometer" *Measurement Science and Technology*, IOP, Bristol, GB, vol. 12, No. 8, pp. 1214-1218, Aug. 1, 2001.

Liu, Xiang, "Line-of-sight absorption of H2O vapor: gas temperature sensing in uniform and non-uniform flows," Ph.D. Dissertation, Department of Mechanical Engineering, Stanford University Jun. 2006.

U.S. Appl. No. 11/715,599, filed Mar. 7, 2007, X. Zhou.
U.S. Appl. No. 60/853,313, filed Oct. 18, 2006, X. Zhou.
U.S. Appl. No. 11/818,617, filed Jun. 14, 2007, X. Zhou.

* cited by examiner

US 7,586,094 B2

BACKGROUND COMPENSATION BY MULTIPLE-PEAK MEASUREMENTS FOR ABSORPTION SPECTROSCOPY-BASED GAS SENSING

RELATED APPLICATION

The present patent application claims priority to U.S. Patent Application Ser. No. 60/898,475, filed on Jan. 30, 2007 and entitled "Background Compensation by Multiple-Peak Measurements for Absorption Spectroscopy-Based Gas Sensing," the entire disclosure of which is incorporated by reference herein.

TECHNICAL FIELD

The subject matter described herein relates to absorption spectroscopy-based measurements of gas mixtures.

BACKGROUND

Interfering absorption from background gases in a gas stream may limit detection sensitivity or even prevent detection of trace gas contaminants for absorption spectroscopy-based gas sensing systems. Among other potential problems, an inability to sensitively detect critical trace gas contaminants can present risks of serious human health and environmental hazards; damage to machinery; increased production costs; and/or degradation of product quality and product value in industrial, chemical, medical, pharmacological, and energy applications. For example, for moisture detection in natural gas (NG), it can be difficult to find a water vapor absorption transition which is totally free of background absorption interference from methane ($CH_4$), the predominant background gas in the NG stream.

SUMMARY

In one implementation of the current subject matter a method includes quantifying a target absorption of light in a gas sample at a target wavelength and a reference absorption of light in the gas sample at a reference wavelength. The gas sample includes a target analyte having a resolvable target spectral feature at the target wavelength and a background reference analyte having a resolvable background spectral feature at the reference wavelength as well as an interfering background spectral feature at the target wavelength. An inferred background reference analyte absorption of the background reference analyte is calculated at the target wavelength using a background gas adjustment factor that relates measured light absorption at the reference wavelength to light absorption by the background reference analyte at the target wavelength. A target analyte concentration is calculated in the gas sample by adjusting the target absorption using the inferred background reference analyte absorption to determine a calculated target analyte absorption at the target wavelength.

In another interrelated implementation, an apparatus includes a light source configured to provide a light beam that includes a target wavelength and a reference wavelength. The target wavelength is selected to approximately coincide with a target analyte resolvable spectral feature in a gas sample, and the reference wavelength is selected to approximately coincide with a background reference analyte resolvable spectral feature in the gas sample. The background reference analyte also has an interfering spectral feature in the vicinity of the target wavelength. The apparatus also includes a photodetector configured to measure a target absorption at the target wavelength and a background absorption at the reference wavelength as well as a control unit coupled to the photodetector and configured to calculate an inferred background reference analyte absorption at the target wavelength based on a measured absorption at the reference wavelength. The control unit uses the inferred background reference analyte absorption to calculate the target analyte absorption at the target wavelength and thereby quantify the concentration of the target analyte in the gas sample.

In other optional variations the gas sample can further include a second background reference analyte that has a second interfering spectral feature at the target wavelength and also a second background spectral feature at a second background reference wavelength. The method can optionally include quantifying a second reference absorption of light in the gas sample at the second reference wavelength. An inferred second background reference analyte absorption of the second background reference analyte at the target wavelength can be calculated using a second background gas adjustment factor that relates measured light absorption at the second reference wavelength to light absorption by the second background reference analyte at the target wavelength. The target analyte concentration in the gas sample can be calculated by further adjusting the target absorption using the inferred second background reference analyte absorption to determine the calculated target analyte absorption at the target wavelength.

In optional variations, an apparatus or method can also include containing the gas sample in a sample cell. The sample cell can be positioned such that light from the light source passes through the gas sample. The control unit can optionally calculate the inferred background reference analyte absorption of the background reference analyte at the target wavelength using a background gas adjustment factor that relates measured light absorption at the reference wavelength to light absorption by the background reference analyte at the target wavelength. The background gas adjustment factor can optionally be based on calibration data collected for one or more calibration samples containing the background reference analyte.

In other optional variations of the above-described implementations the target analyte can be chosen from a group consisting of water vapor, hydrogen sulfide, hydrogen chloride, hydrogen fluoride, hydrogen bromide, hydrogen iodide, hydrogen cyanide, ammonia, carbon dioxide, carbon monoxide, acetylene, methyl-acetylene, propadiene, sulfur dioxide, mercaptans, carbonyl sulfide, carbon disulfide, ethane, propane, ethylene, propylene, phosgene, arsine, phosphine, and oxygen, and the background reference analyte comprises one or more gases selected from hydrocarbons fluoro-carbons, chloro-carbons, freons, water vapor, ammonia, carbon monoxide, carbon dioxide, nitrogen, oxygen, chlorine, hydrogen, methane, ethane, propane, butane, pentane, hexane, septane, octane, nonane, decane, ethylene, propylene, butene, acetylene, vinyl-chloride, acrylonitrile, and acetonitrile.

If the target analyte is water vapor, and the background reference analyte is methane, and the target wavelength and reference wavelength can optionally be chosen from groups including approximately 1392.54 nm for the target wavelength and approximately 1392.36 nm, approximately 1392.41 nm, or approximately 1392.55 nm for the reference wavelength; approximately 1395.00 nm for the target wavelength and approximately 1395.03 nm or approximately 1394.99 nm for the reference wavelength; approximately 1854.03 nm for the target wavelength and approximately 1853.15 nm for the reference wavelength; approximately 1877.1 nm for the target wavelength and approximately 1877.05 nm for the reference wavelength; and approximately 1877.1 nm for the target wavelength and approximately 1876.99 nm for the reference wavelength. If the target analyte is carbon dioxide and the background reference analyte is ethane, the reference wavelength can optionally be approximately 2001.94 nm, and the target wavelength can optionally be chosen from a group including approximately 2000.23 nm, approximately 2000.66 nm, approximately 2001.56 mm, approximately 2003.50 nm, approximately 2004.02 nm, and approximately 2004.55 nm. If the target analyte is carbon monoxide and the background reference analyte is methane, the target wavelength and reference wavelength can optionally be chosen from groups including approximately 2389.28 nm for the target wavelength and approximately 2389.32 nm for the reference wavelength approximately 2381.00 nm for the target wavelength and approximately 2381.10 nm for the reference wavelength, approximately 2365.55 nm for the target wavelength and approximately 2365.48 nm for the reference wavelength, approximately 2663.13 nm for the target wavelength and approximately 2363.19 nm for the reference wavelength, approximately 2360.75 nm for the target wavelength and approximately 2360.68 nm for the reference wavelength, approximately 2326.83 nm for the target wavelength and approximately 2326.78 nm or approximately 2326.92 nm for the reference wavelength, approximately 2323.63 nm for the target wavelength and approximately 2323.55 nm or approximately 2323.65 nm for the reference wavelength, and approximately 2313.71 nm for the target wavelength and approximately 2313.67 nm for the reference wavelength.

In other optional variations, light absorption data can be collected at the target wavelength and the reference wavelength for one or more calibration gas samples having known concentrations of the target analyte and/or the background reference analyte, and the background gas adjustment factor can be generated based on the light absorption data. The light can be provided by one or more light sources that include one or more of a tunable diode laser, a tunable quantum cascade (QCL) semiconductor laser, a tunable horizontal cavity laser, a tunable vertical cavity surface emitting semiconductor laser (VCSEL), or a means for nonlinear frequency generation of tunable light. Light from at least one light source can be directed through the gas sample. The light from the at least one light source can include the target wavelength and the reference wavelength. The one light source can provide a light beam having a spectrally narrower emission bandwidth than the target analyte absorption and/or the reference analyte absorption. In other options, light from a first light source and a second light source can be passed through the gas sample. The light from the first light source can include the target wavelength and the light from the second light source can include the reference wavelength. A path length of light absorption for the first and the second light sources can be substantially identical. Light from the first and the second light sources can be multiplexed into a single physical path through the gas sample. Different wavelength modulation frequencies can optionally be used for the first and second light sources. The target wavelength and the reference wavelength can optionally be wavelength modulated to produce a harmonic output that is analyzed by a control unit or processor to calculate the background gas adjustment factor and the target analyte concentration. A current and/or a voltage output from a photodetector upon which the light at the target wavelength and the reference wavelength impinge can be measured and the measured current and/or voltage output can be analyzed by the control unit or processor to calculate the background gas adjustment factor and the target analyte concentration.

Among other possible advantages, the subject matter described herein may be used to provide real time compensation of variations in the absorption background for absorption spectroscopy-based gas sensing. By using the techniques and systems described herein, the influence of the background variations on the target gas concentration measurements can be significantly reduced or eliminated, and thus the measurement accuracy can be greatly improved. Complicated calibration experiments and correlations are not required, so that substantial simplification and reductions in the processing resources required for intensive calculations and software complexity can be implemented. Target analyte concentration measurements can be corrected to account for the interference of background analyte absorption for background analytes present at concentrations below those of the target analyte, at or near the concentration of the target analyte, and greater than the concentration of the target analyte. One or more background analytes can be corrected for if necessary.

One or more of the potential benefits of the presently disclosed subject matter may be realized in a number of combinations of gas-phase target analyte and a range of background gases, potentially over the whole optical spectrum from 100 nm to 100,000 nm. Background absorption interferences arising from multiple background gases present in the gas mixture can be corrected for as well.

DESCRIPTION OF THE DRAWINGS

This disclosure may be better understood upon reading the detailed description and by reference to the attached drawings, in which.

DETAILED DESCRIPTION

The presently disclosed subject matter includes methods, techniques, systems, structures, and articles of manufacture that may be used to adjust a spectroscopic measurement of a target analyte concentration to compensate for light absorption by one or more background analytes. Absorption of one or more background analytes in a gas sample can be measured at a reference wavelength and then used to infer or otherwise calculate the contribution of light absorption by the background analyte or analytes at a target wavelength where absorption of the target analyte is measured. For purposes of this disclosure, the target wavelength is the wavelength selected for the analyte measurement. The target wavelength can optionally be at or near the peak of a background analyte absorption transition as discussed in greater detail below. One or more reference wavelengths are selected and used to infer the contribution of background gases in a sample mixture to absorption observed at the target wavelength.

If the background gas concentration is relatively constant with time, the absorption at the target wavelength that is due to background analytes in a gas sample can be calibrated in advance and subtracted from the measured total absorption at the target wavelength to compensate for background analyte absorption. However, the background analyte concentration of a gas being analyzed can change for a variety of reasons. In one illustrative example, the methane concentration in a NG stream may change due to switching between NG sources or a change in the mixing ratio of different NG sources, which is a common occurrence for NG pipelines. To address this issue, the presently disclosed subject matter can monitor changing absorption due to background gases in a gas sample or gas stream and can compensate in real-time in order to achieve accurate and reliable measurement results for a target analyte.

Figure 1:
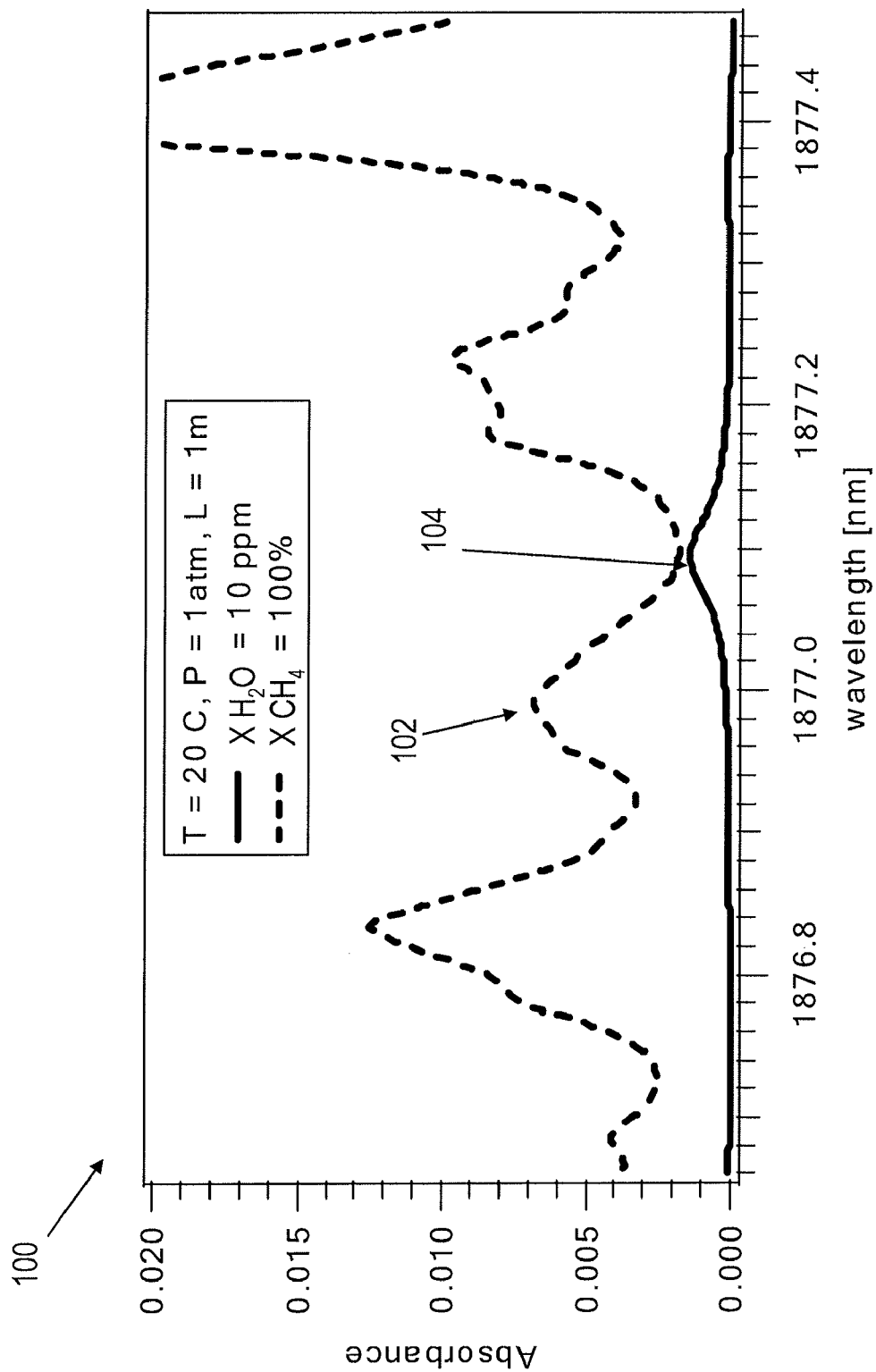
FIG. 1 is a chart showing the simulated absorption spectra of water vapor and methane in the spectral region around 1877 nm.

FIG. 1 is a chart 100 showing the absorption intensity curve 102 of 10 ppm of water superimposed on the absorption intensity curve 104 of 100% methane. As can be seen from FIG. 1, the CH4 background absorption at this H2O absorption peak near 1877.1 nm is not negligible in methane concentrations typical of natural gas or liquid natural gas (for example in the range of about 70% to 100%). This background absorption can lead to a deviation in the measured water vapor concentration that is inferred from the measured absorption at 1877.1 nm relative to the actual water vapor concentration in the sample gas. Similar background interference issues can occur for a wide variety of gas mixtures.

Figure 2:
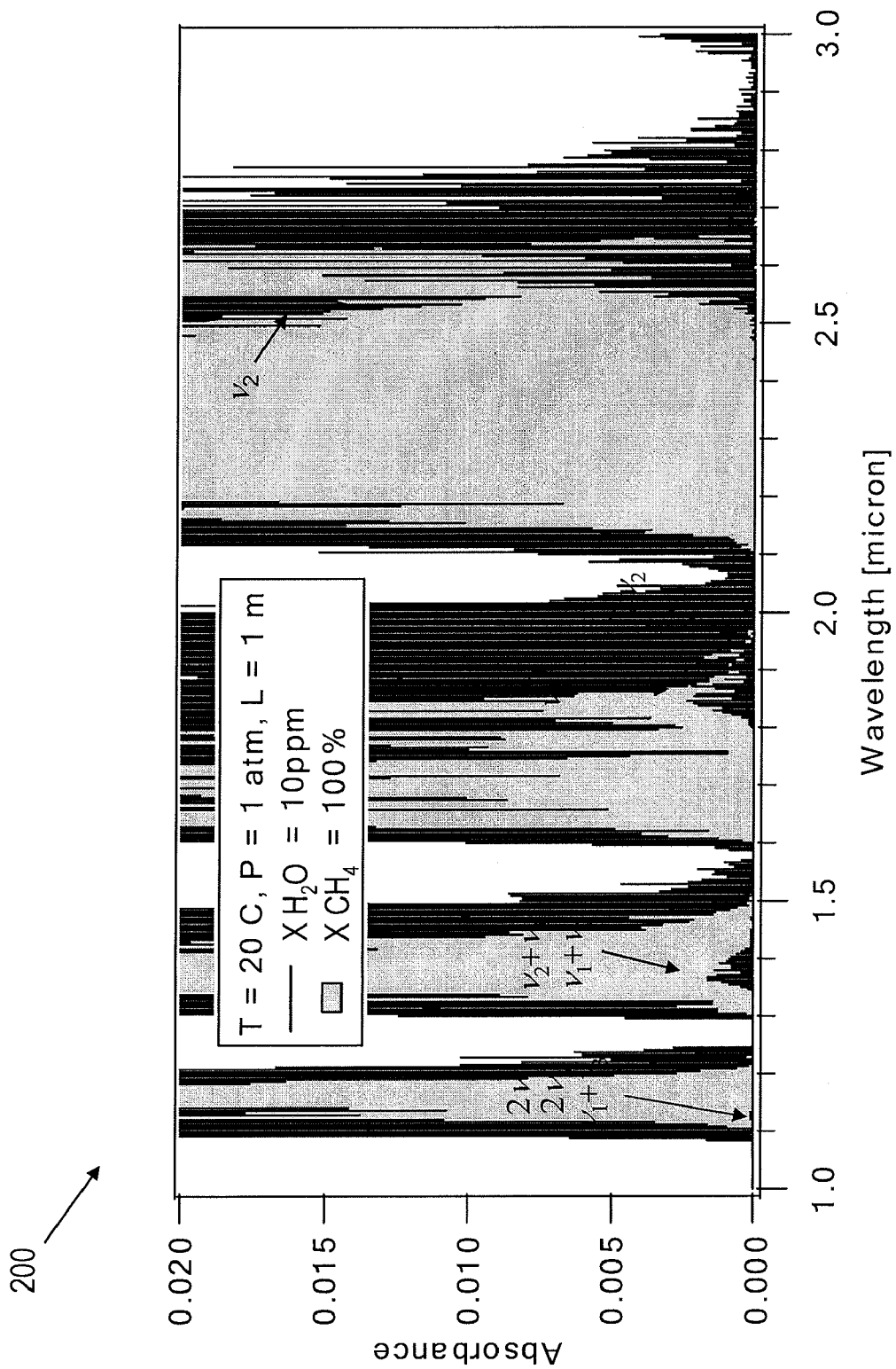
FIG. 2 is a chart showing the simulated absorption spectra of water vapor and methane in the near-infrared spectral region of 1 to 3 microns.

The $H_2O$ transition at 1877.1 nm has been used for moisture detection in natural gas pipelines, for example, as described in U.S. Pat. No. 6,657,198, the contents of which are hereby incorporated by reference. Even though this transition has the smallest $CH_4$ absorption interference among all of the water transitions available within the overtone and combinational water absorption bands in the 1300 nm-2000 nm near-infrared (NIR) spectral region, moisture detection sensitivity can nonetheless be limited due to the background methane absorption. The spectral region from 1300 nm-2000 nm, where robust tunable diode lasers are available, covers the $2 v_1$, $2 v_3$, and $v_1 + v_3$ water absorption bands centered around 1400 nm, and the $v_1 + v_2$ and $v_2 + v_3$ bands centered around approximately 1900 nm, as shown in the chart 200 of FIG. 2.

Figure 3:
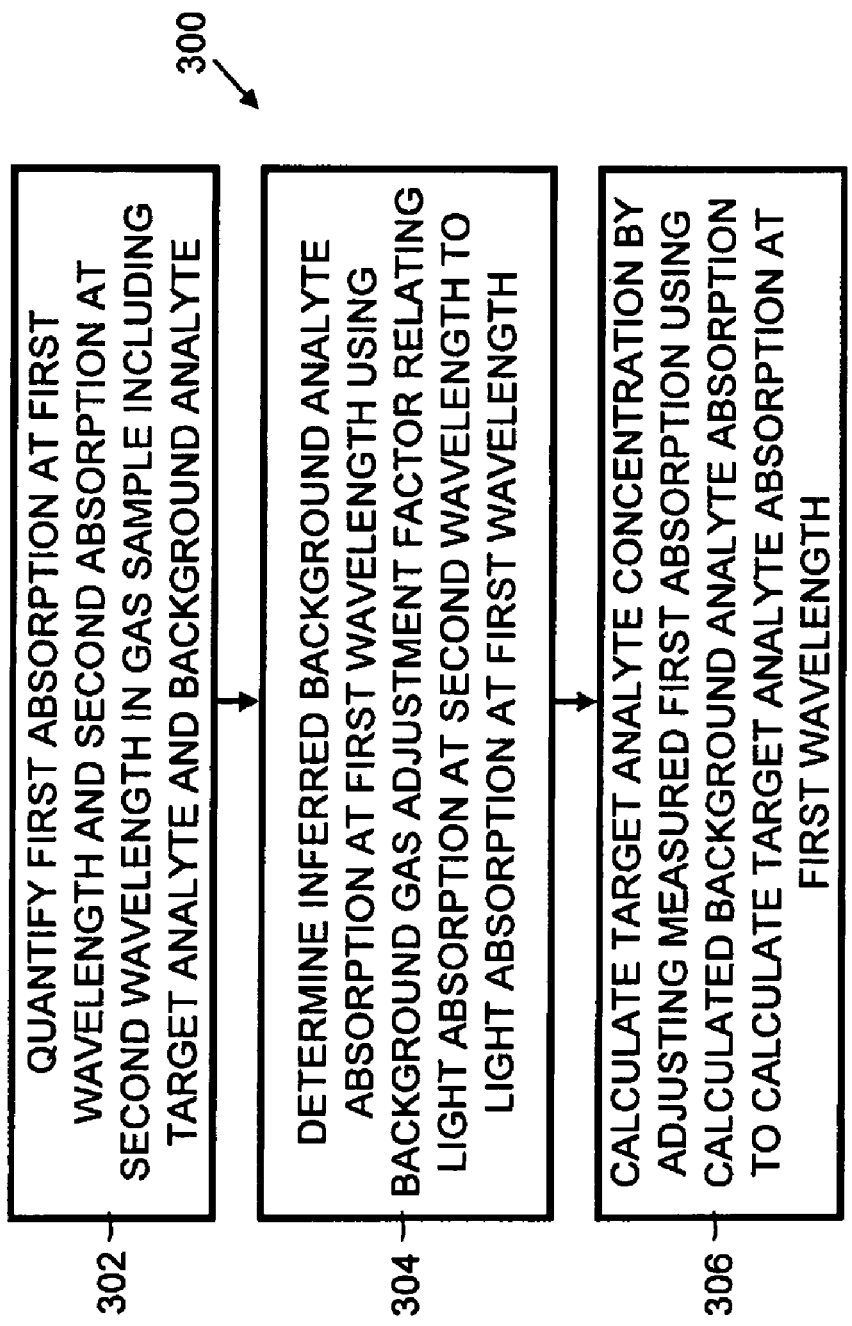
FIG. 3 is a process flow diagram illustrating a method for determining a target analyte concentration by compensating for the absorption effects of a background analyte.

FIG. 3 shows a process flow chart 300 of a method for measuring the concentration of a target analyte in a gas mixture. At 302, a target absorption is quantified at a target wavelength and a reference absorption is quantified at a reference wavelength for a gas sample that includes a target analyte and at least one background analyte that may have a spectral absorption feature at the target wavelength. An inferred background analyte absorption at the target wavelength is determined, at 304, using a background gas adjustment factor or function that relates the measured light absorption at the reference wavelength to an amount of light expected to be absorbed by the background analyte at the target wavelength. In some implementations, the background compensation factor or function can be accurately represented by a $1^{st}$ order polynomial (a linear function). Higher order polynomials or other mathematical functions can also be used for the background compensation factor or function. The absorption strength of the background analyte at the target wavelength can then be calculated using the inferred absorption strength of the background analyte at the reference wavelength using the background gas adjustment factor.

Referring again to FIG. 3, the target analyte concentration is calculated, at 306, by adjusting the measured first absorption using the calculated background analyte absorption. This adjustment can be accomplished by calculating the background absorption contribution to the target absorption measured at the target wavelength and subtracting the calculated background absorption from the measured first absorption. The background gas adjustment factor can be a direct mathematical relationship between an observed absorption at the reference wavelength and a predicted absorption by the background analyte at the target wavelength. Alternatively, the concentration of one or more background analytes can be determined, either based on the observed absorption at the reference wavelength or by some other method that provides real time or semi-real time measurements of the concentration of one or more background analytes. The one or more background analyte concentrations can then be converted to an inferred background analyte absorption at the target wavelength by comparison to one or more reference spectra and/or pre-determined lookup tables.

In conjunction with a method such as is shown in FIG. 3, light for the absorption measurements can be provided in a single scan from a tunable laser with a scan range that includes both the target and reference wavelengths. Alternatively, two or more lasers can be used to provide the target and one or more reference wavelengths. This arrangement can allow for a broader spacing between the target and reference wavelengths than might be possible with a single light source. A vertical cavity surface emission laser (VCSEL) can be used to provide a relatively broad scan range that can be used for target and reference peaks that are not as close to one another. An external cavity semiconductor laser can be used to provide a large scan range, covering between 0.1 nm and 250 nm. Other light sources can include edge emitting single frequency diode lasers, vertical cavity surface emitting lasers (VCSEL), quantum cascade lasers, horizontal cavity surface emitting lasers (HCSEL), tunable diode lasers that are tuned by either current or temperature adjustments or by adjustment of dispersive optical elements, including prisms and diffraction gratings, and the like. For tunable lasers, either direct lasing or harmonic frequency modulation techniques can be used. Broadband lasers can also be used. Tunable dye lasers, solid state lasers and color center lasers can also be used. Any light source can be used which has a spectral line width narrower than the absorption line width of the respective target analyte.

The sample gas containing the target analyte and background reference gas can in some implementations have a pressure in a range of approximately 1 Pa to $10^7$ Pa, while the target analyte can in some implementations have a concentration of at least 1 part per trillion by volume. In some implementations, the light with the first and the second wavelength can optionally be delivered to the gas sample by an optical fiber arrangement or a free space optical arrangement. The light source can optionally provide one or more wavelengths between approximately 100 nm and approximately 100,000 nm. The difference in wavelength of light absorption between the target analyte and the background reference absorption can in some implementations be greater than approximately 0.0001 nm.

Figure 4:
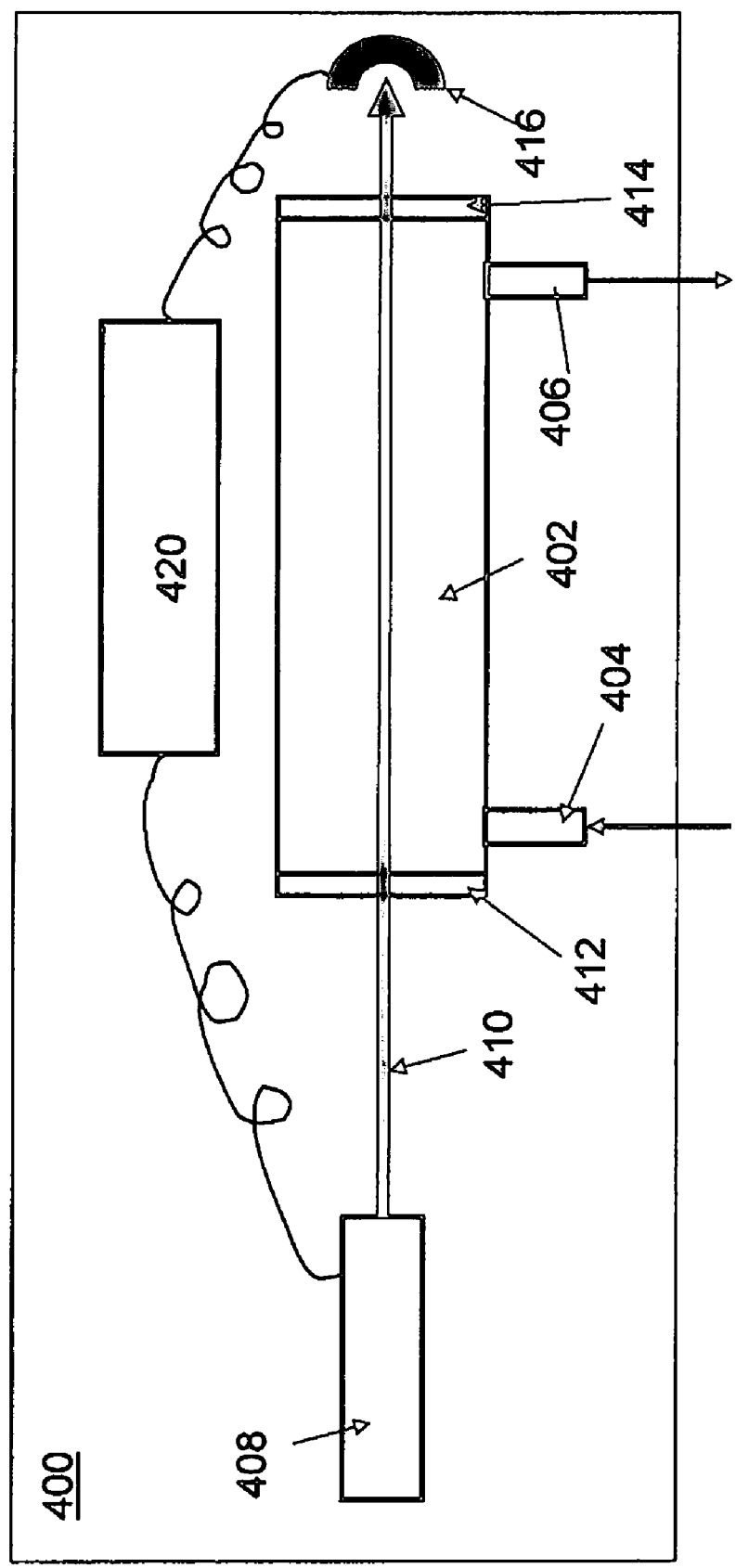
FIG. 4 is a schematic diagram of an analyzer according to one implementation of the subject matter described herein.

FIG. 4 is a schematic diagram showing an analyzer 400 that implements various aspects of the current subject matter. In this implementation, a gas sample is contained within a sample cell 402. The gas sample can be directed into the sample cell 402 via an inlet 404 and flushed from the sample cell 402 via an outlet 406. In some variations, the inlet 404 and the outlet 406 can include valves that can seal the inner volume of the sample cell 402 to obtain a static measurement of a fixed volume of gas. If there are no inlet and outlet valves, or if the inlet and outlet valves are open, the system can be used in a continuous or semi-continuous flow mode, such as for example to continuously or semi-continuously monitor the concentration of a target analyte in a flowing gas stream. For continuous or semi-continuous operation, all or part of a gas stream can be directed into the sample cell 402 via the inlet 404 and flushed out of the sample cell 402 via the outlet 406 by the flow of the gas. Flow through the sample cell 402 can be caused by a pressure differential created by a pump or some other mechanism.

A light source 408 that provides light with at least a target wavelength and a reference wavelength generates a continuous or pulsed beam 410 that is directed through the gas volume of the sample cell 402. The light source can be one of those discussed above, or other comparable sources of light that are amendable to quantification of the amount of light absorbed as it passes through the gas sample. In the example shown in FIG. 4, the sample cell includes windows 412 and 414 that allow the light beam 410 to enter and exit the cell. Other configurations are possible, including but not limited to those described in co-pending U.S. patent application Ser. No. 11/715,599, the disclosure of which is incorporated by reference in its entirety. The sample cell 402 may be a single pass design in which the light beam 410 from the light source 408 passes once through the gas volume of the sample cell 402 before exiting the sample cell 402. In this configuration, the optical path length is effectively the length of the sample cell 402. It is also possible to use one or more mirrors that reflect the light beam 410 such that it passes through the sample volume more than once before exiting the sample cell 402. A Herriot cell (described in full detail in U.S. patent application Ser. No. 11/715,599), in which the light beam 410 is reflected between two spherical mirrors numerous times to create a very long optical path length, may also be used. The optical path length can be selected based on the strength of the absorption features being used in a measurement and the concentration of the gases being analyzed. Alternatively, a White cell, an off axis optical resonator cavity, and an on-axis optical resonator cavity can be used.

The light beam 410 is directed onto a photodetector or other device for quantifying the intensity of incident light 416 as the light beam exits the sample cell 402. The photodetector 416 can be electronically coupled to a control unit 420 that can optionally also be electronically coupled to the light source 408 as shown in FIG. 4. The control unit 420 can include one or more processors coupled to a memory that stores instructions in computer readable code. When executed on the processor or processors, the instructions can implement a method, such as for example that described above, to analyze the absorption at the reference wavelength to infer and compensate for the absorption at the target wavelength that is due to the background analyte. Once the absorption at the target wavelength is so compensated, the control unit 420 can calculate the target analyte concentration.

If the control unit 420 is electronically connected to the light source 408, it can optionally control the light source. For example, if the light source 408 is a tunable diode laser, such as one of those described in U.S. patent application Ser. No. 11/715,599, the control unit can control the scan and modulation rates of the driving current for the light source and also interpret the direct current measurements by the photodetector 416 to convert them to modulated 2 f values.

The reference wavelength can be chosen to approximately coincide with a background analyte absorption feature that is relatively free of interfering absorption features of other components of the gas mixture. The target wavelength can be chosen to at least approximately coincide with a target analyte absorption feature. In one example, the target analyte has an absorption line between 100 nm and 100,000 nm and the interfering background analyte has at least the one reference wavelength within ±500 nm of the target analyte wavelength. The background analyte can have an additional absorption feature that interferes with a direct spectroscopic measurement of target analyte absorption at the target wavelength using conventional spectroscopic measurements. The reference wavelength selection can be based on availability of an absorption transition of the background analyte. This selection can be based on one or more criteria, including but not limited to strength of the absorption line for the background analyte, relative isolation of the absorption transition of the background analyte from absorption features of the target analyte and also from other background gases. The strength of the absorption transition of the background analyte can be selected to be not so strong that it results in an optically opaque or nearly opaque condition. In other words, the background analyte absorption at the reference wavelength should not be so strong that no light at that wavelength is transmitted through the sample gas.

Figure 5:
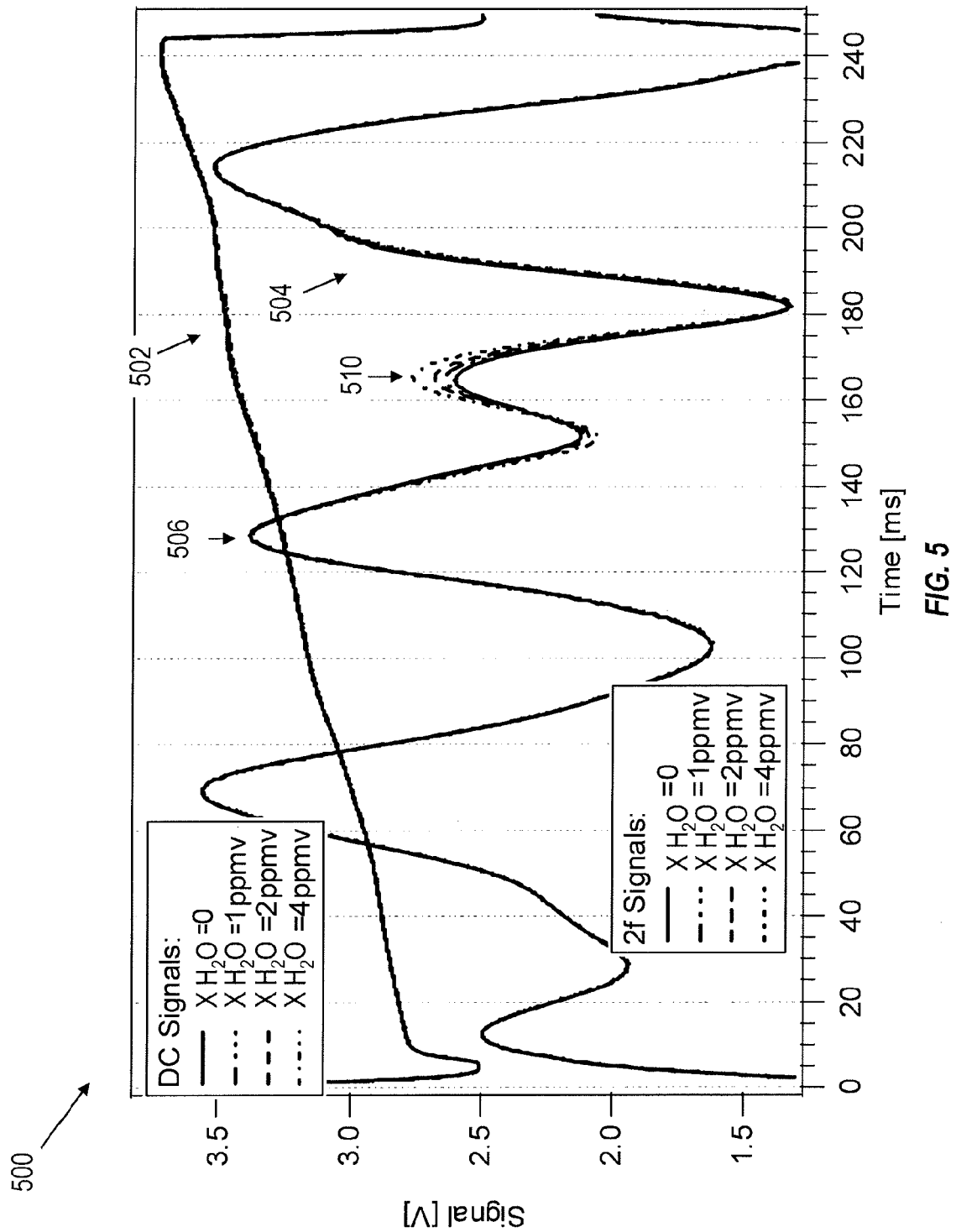
FIG. 5 is a chart showing the measured direct current and 2 f signals at different moisture levels with a background of predominantly $CH_4$.

In one example, moisture concentrations in natural gas can be measured using the presently disclosed subject matter with a first wavelength of 1877.1 nm, which corresponds to a water absorption transition. The second wavelength used to calculate the background gas adjustment factor can be selected to approximately coincide with the absorption peak of $CH_4$ on the blue side of the water absorption peak at approximately 1877.05 nm, as shown in FIG. 5. FIG. 5 is a chart 500 that illustrates selection of the target and reference wavelengths for measurement of water vapor in natural gas containing high concentrations of methane. The direct current detector response curves 502 and 2 f modulated signal response curves 504 measured for laser scans from a tunable diode laser in the region of 1877.1 nm wavelength are shown for multiple gas samples with different, known, water vapor mole fractions (X $H_2O$) and a constant concentration of the background analyte (in this example methane). As FIG. 5 shows, the absorption response at the reference wavelength 506 is substantially constant despite variation of the water vapor concentration from 0 to 4 ppmv. However, the detector response signal at the target wavelength 510 shows substantial sensitivity to changes in the water vapor concentration. For water vapor in methane, other pairs of target and reference wavelengths including but not limited to 1392.54 nm for the target wavelength, and approximately 1392.36 nm, approximately 1392.41 nm, or approximately 1392.55 nm for the reference wavelength; approximately 1395.00 nm for the target wavelength and approximately 1395.03 nm or approximately 1394.99 nm for the reference wavelength; approximately 1854.03 nm for the target wavelength and approximately 1853.15 nm for the reference wavelength; and approximately 1877.1 nm for the target wavelength and approximately 1876.99 nm for the reference wavelength can also be used. Other appropriate target and reference wavelength pairings can be used for other combinations of target and background analytes in a specific gas mixture.

As noted above, many other mixtures of background and target gases can be analyzed as described herein. For example, the target analyte can optionally be one of water vapor, hydrogen sulfide, hydrogen chloride, ammonia, carbon dioxide, carbon monoxide, acetylene, methyl-acetylene, propadiene, and oxygen in a mixture containing one or more hydrocarbon background analytes including but not limited to methane, ethane, propane, butane, pentane, hexane, septane, octane, nonane, decane, ethylene, propylene, acetylene, vinyl-chloride monomers, acrylonitrile, and acetonitrile. The presently described subject matter can also work for gas mixtures with other than hydrocarbon backgrounds, including but not limited to fluorocarbons, chlorocarbons, $CO_2$, CO and symmetrically diatomic and mono-atomic gases and any mixtures thereof.

For $CO_2$ as the target analyte and ethane as the background analyte, possible target wavelengths include, but are not limited to, approximately 2000.23 nm, approximately 2000.66 nm, approximately 2001.56 nm, approximately 2003.50 nm, approximately 2004.02 nm, and approximately 2004.55 nm, and the reference can be, among other possibilities, approximately 2001.94 nm.

For CO as the target analyte and methane as the background analyte, possible target wavelength/reference wavelength pairs include, but are not limited to, approximately 2389.28 nm for the target wavelength and approximately 2389.32 nm for the reference wavelength, approximately 2381.00 nm for the target wavelength and approximately 2381.10 nm for the reference wavelength, approximately 2365.55 nm for the target wavelength and approximately 2365.48 nm for the reference wavelength, approximately 2663.13 nm for the target wavelength and approximately 2363.19 nm for the reference wavelength, approximately 2360.75 nm for the target wavelength and approximately 2360.68 nm for the reference wavelength, approximately 2326.83 nm for the target wavelength and approximately 2326.78 nm or approximately 2326.92 nm for the reference wavelength, approximately 2323.63 nm for the target wavelength and approximately 2323.55 nm or approximately 2323.65 nm for the reference wavelength, and approximately 2313.71 nm for the target wavelength and approximately 2313.67 nm for the reference wavelength.

Figure 6:
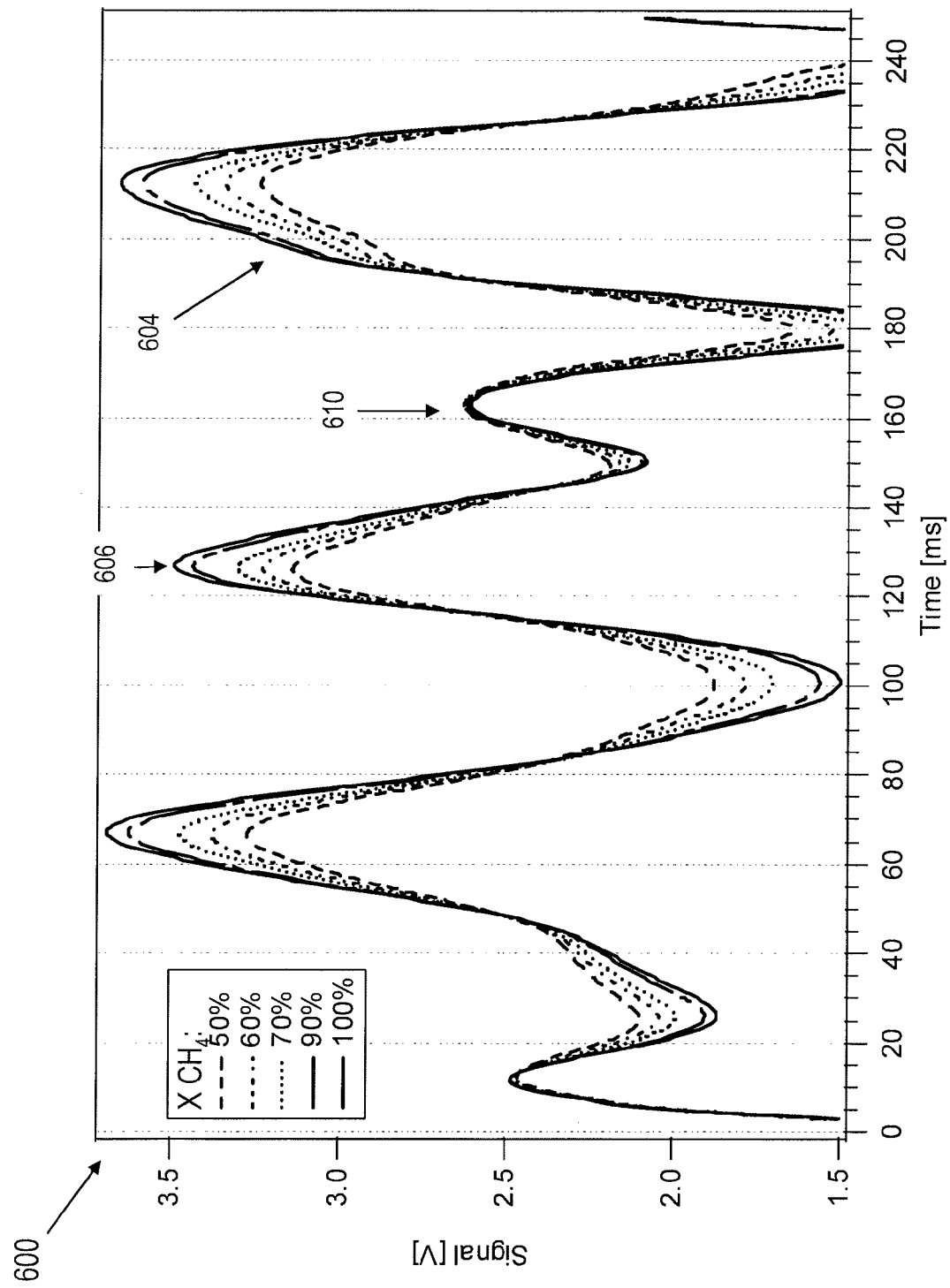
FIG. 6 is a chart showing measured 2 f signals when flowing a dried mixture of $CH_4$ and $N_2$ through an analyzer as described herein.

FIG. 6 is a chart 600 showing 2 f modulated detector response curves 604 for a similar comparison to that in FIG. 5. Here, the target analyte (water vapor) concentration is kept constant for a number of gas samples which have varying concentrations of the background analyte (methane). In this case, the detector response at the reference wavelength 606 varies with changing background concentration, but the response at the target wavelength 610 is approximately constant despite a factor of 2 change in the background gas concentration (from a methane mole fraction of 50% to 100%). Using absorption peak relationships such as those shown in FIG. 5 and FIG. 6 for a background and target analyte in a gas mixture, the concentration of the background analyte can be inferred based on the observed absorption at the reference wavelength.

In one implementation, one or more calibration gas samples, each containing a known concentration or mole fraction of the background analyte, are analyzed to determine absorption at both the target wavelength and the reference wavelength. A correlation function or other mathematical relationship may be developed based on these calibration measurements to relate absorption due to the background analyte measured at the reference wavelength to absorption due to the background analyte measured at the target wavelength. In one variation, calibration samples can be used to determine a mathematical relationship between the background analyte concentration and the absorption at the second wavelength and also between the background analyte concentration and the absorption of the background analyte at the first wavelength. Then, these relationships can be used during a gas sample analysis to first determine the background analyte concentration based on measured absorption at the second wavelength and then convert the determined background analyte concentration into an expected background analyte absorption at the first wavelength. The expected background analyte concentration at the first wavelength can then be subtracted from the measured absorption at the first wavelength to yield an inferred absorption at the first wavelength that is due to the target analyte. In another alternative, a function may be determined based on the calibration samples that directly relate observed absorption at the second wavelength to expected absorption by the background analyte at the first wavelength.

As illustrated by the data shown in FIG. 5 and FIG. 6, analysis of water vapor concentrations in natural gas containing substantial concentrations of methane may be improved using the disclosed subject matter. Calibrations of the absorption strength of methane at both a target wavelength and a second or background wavelength can be used to generate a background gas adjustment factor or function that relates the absorption measured for a gas sample at the second wavelength to an expected absorption at the first wavelength that is attributable to the methane in the sample. This expected methane absorption at the first wavelength can be subtracted from the measured absorption at the first wavelength to compensate for background absorption that would otherwise introduce errors into the quantification of water vapor concentrations in the gas sample. In the example of water vapor in methane, the 2 f peak-to-valley heights (or 2 f peak heights) at the labeled wavelengths can be measured when varying the $CH_4$ mole fractions from 50% to 100% as shown in FIG. 6. Similarly, calibrations can generally be made for the absorption characteristics of the target analyte at least at the target wavelength and also optionally at the reference wavelength.

In a further variation, one or more additional background analytes can also be compensated for in a similar manner. A reference wavelength for each background analyte is identified, and the procedure described above for a single background analyte is followed for each background analyte. A calculated absorption at the target wavelength is inferred for each background analyte based on the measured absorption at that background analyte's reference wavelength. For example, a first reference wavelength can be used to infer the contribution of a first background analyte to the observed absorption at the target wavelength and a second reference wavelength can be used to infer the contribution of a second background analyte to the observed absorption at the target wavelength. If there are three potentially interfering background analytes in the gas mixture, a third reference wavelength can be used to infer the contribution of a third background analyte to the observed absorption at the target wavelength, and so on for any number of potentially interfering background analytes. The criteria for picking each reference wavelength are the same as those discussed above for a single background analyte. For example, if there are two background analytes that interfere at the wavelength to be used for the target wavelength, the first and the second reference wavelengths, which could also be labeled as the second and third wavelengths can be used such that the second wavelength is used to infer a calculated absorption for the first background analyte at the target wavelength and the third wavelength is used to infer a calculated absorption for the second background analyte at the target wavelength.

A method or analyzer according to the disclosed subject matter can be implemented by measuring the absorption of the background gas at the reference wavelength either simultaneously or in parallel with the measurement of the total absorption at the target wavelength. This can be accomplished in some implementations using devices similar to those described in U.S. Pat. Nos. 6,657,198, 7,132,661, and U.S. Pat. App. Ser. No. 60/853,313, and Ser. No. 11/818,617, all of which are incorporated by reference. For a simultaneous measurement, and when the reference wavelength is close enough to the target wavelength, both wavelengths can be covered by the scanning range of a single tunable laser. A single tunable laser light source, such as a tunable diode laser, which can include but is not limited to a distributed feedback (DFB) laser, a vertical cavity surface emitting laser (VCSEL), a horizontal cavity surface emitting laser (HCSEL), may provide light at both the target wavelength and the reference wavelength. Other types of lasers and light sources providing a light beam which is spectrally narrower than the width of the target or reference analyte absorption line, including but not limited to quantum cascade semiconductor lasers and nonlinear optical frequency generation, can also be used.

In an alternative implementation, an additional light source or sources can be used to measure the background absorption either simultaneously or in parallel with the measurement of the analyte absorption. For simultaneous measurements, light from the two (or more) light sources can be multiplexed into one physical path through the sample gas by time-division multiplexing, wavelength-division multiplexing, or frequency-division multiplexing, such as for example is described in X. Liu, Ph.D dissertation, Stanford University June 2006, "Line-of-sight of absorption of $H_2O$ vapor: Gas temperature sensing in uniform and non-uniform flows", the contents of which are hereby incorporated by reference. In another implementation, two light sources, a first providing the target wavelength and a second providing the reference wavelength, may be oriented with non-coinciding paths through a gas sample. If the gas sample is properly mixed, measurement of absorption at the reference wavelength can be used as described above to compensate for background absorption occurring at the target wavelength.

As noted above, the target or first wavelength and the reference or second wavelength can be selected to be close enough so that both wavelengths can be well covered by the scanning range of a single tunable diode laser. One specific example of this is the use of the $H_2O$ transition at 1877.1 nm as the target wavelength and its neighbor $CH_4$ transition at 1877.05 nm as the reference wavelength, as described above for moisture detection in natural gases. The absorption response for varying methane concentrations with constant water vapor and for varying water vapor concentrations with constant methane are shown in FIG. 4 and FIG. 5, respectively. For moisture detection in natural gases, a $H_2O$ transition, for example in the 1.4 micron band, or the 1.9 micron band, or the 2.7 micron band, can be used as the target wavelength while a neighbor or nearby $CH_4$ transition can be used as the reference wavelength. For HCl detection in $H_2$ reformer gas streams, a HCl transition, for example in the 1.7 micron band, can be used as the target wavelength and its neighbor or nearby $CH_4$ transition can be used as the reference wavelength. For $H_2S$ detection in natural gas and other gas streams containing hydro-fluoro and chloro-carbon, a $H_2S$ transition, for example in the 1.5 micron, 1.9 micron, or 2.6 micron band, can be used as the target wavelength and a neighbor or nearby $CH_4$, $C_2H_6$ or $CO_2$ transition can be used as the reference wavelength. Similar techniques can be used for other combinations of one or more target gases, including but not limited to ammonia, acetylene, methyl acetylene, propadiene, HCl, CO, $CO_2$ and moisture in gas streams containing one more background gases that can include but are not limited to ethylene, propylene, methane, ethane, and propane, butane, iso-butane, other alkanes, vinyl-chloride, acrylo-nitrile, and aceto-nitrile. The disclosed subject matter is not limited to the wavelength bands, target gas species, reference gas species and background streams mentioned but is applicable to the whole optical spectrum between 100 nm and 100,000 nm.

Figure 7:
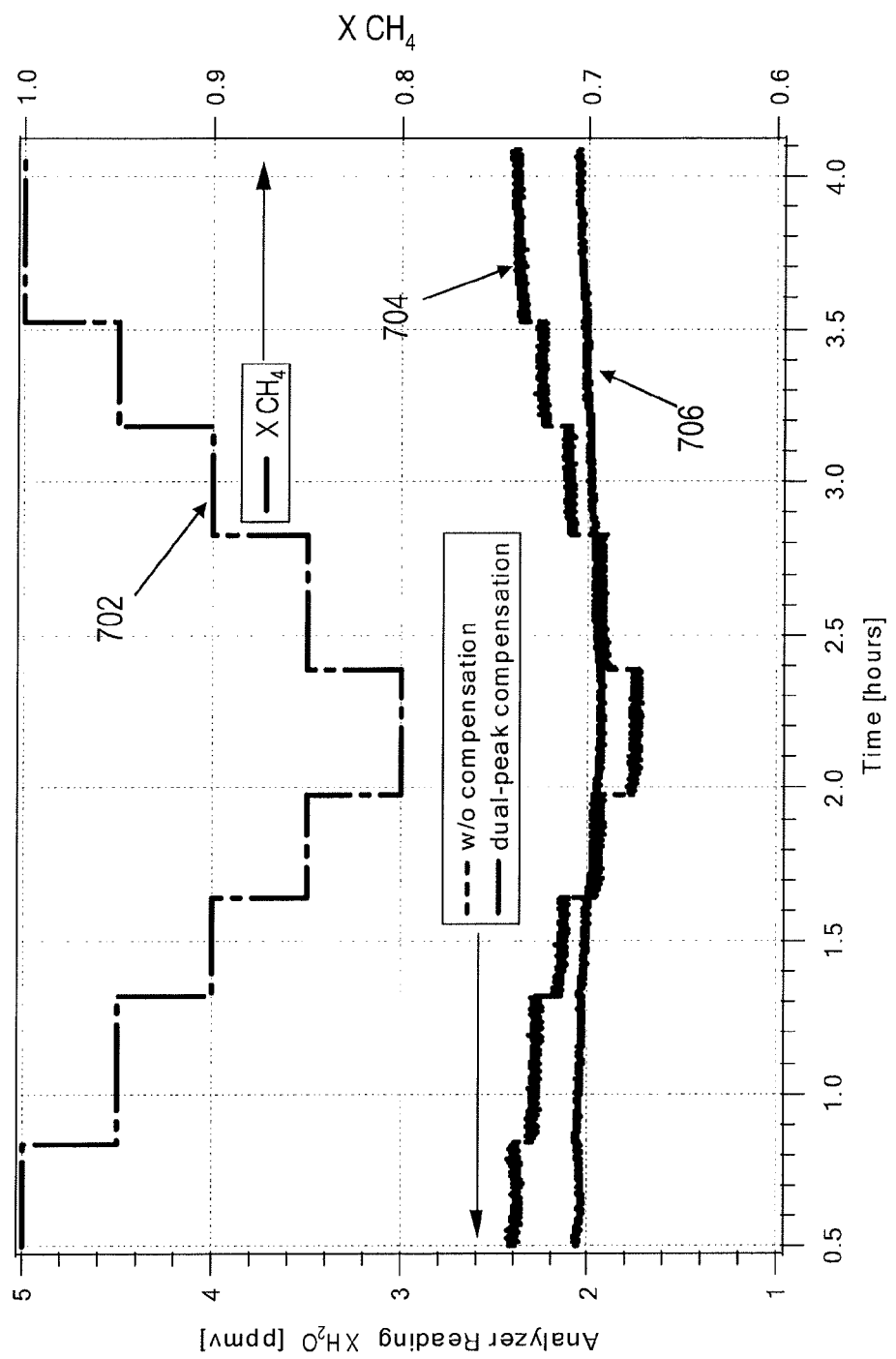
FIG. 7 is a chart showing an analyzer reading for 2 ppmv $H_2O$ in a gas mixture with varying background concentrations of methane.

FIG. 7 shows a comparison of measurement results for an experimental comparison of moisture detection in natural gases using the 1877.1 nm water transition with or without applying the presently disclosed subject matter. Methane mole fractions are shown on the right vertical axis (X $CH_4$) and the water vapor mole fraction (X $H_2O$) is shown on the left axis. During the experiment, the $CH_4$ concentrations were changed from 100% to 80% and then back to 100%, as illustrated by the top trace 702 while the water vapor concentration was held constant. When the subject matter described herein is used to compensate for methane absorption at the target water absorption line (1877.1 nm), the analyzer readings show good repeatability within a tolerance of less than approximately 100 ppbv as shown in the "dual peak compensation" trace 706. Comparatively, if the real-time dual-peak compensation function is removed from the data processing as shown in the "w/o compensation" trace 704, the moisture concentration measured by the analyzer is significantly affected by the $CH_4$ concentration changes in the background gases even though the actual moisture level has not changed.

The subject matter described herein may be embodied in systems, apparatus, methods, and/or articles depending on the desired configuration. In particular, various aspects of the subject matter described herein may be realized in digital electronic circuitry, integrated circuitry, specially designed application specific integrated circuits (ASICs), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, programmable logic devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, implementations of the subject matter described herein can include a computer having a display device (e.g., a CRT (cathode ray tube) or LCD (liquid crystal display) monitor) for displaying information to the user and a keyboard and a pointing device (e.g., a mouse, touchpad or trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

Although a few variations have been described in detail above, other modifications, additions, and implementations are possible are within the scope and spirit of the disclosed subject matter. Features implementing functions may also be physically located at various positions, including being distributed such that portions of functions are implemented at different physical locations. Further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results.

What is claimed:

1. A method comprising:
receiving, at one or more processors, data quantifying a target absorption of light in a gas sample at a target wavelength and a reference absorption of light in the gas sample at a reference wavelength, the gas sample comprising a target analyte and a background reference analyte, the target analyte having a resolvable target spectral feature at the target wavelength, the background reference analyte having a resolvable background spectral feature at the reference wavelength and also an interfering background spectral feature at the target wavelength;
calculating, using at least one of the one or more processors, an inferred background reference analyte absorption of the background reference analyte at the target wavelength using a background gas adjustment factor that relates the reference absorption at the reference wavelength to light absorption at the target wavelength that is due to the background reference analyte; and
calculating, using at least one of the one or more processors, a target analyte concentration in the gas sample by adjusting the target absorption using the inferred background reference analyte absorption to determine a calculated target analyte absorption at the target wavelength.

2. A method as in claim 1, wherein the target analyte is chosen from a group consisting of water vapor, hydrogen sulfide, hydrogen chloride, hydrogen fluoride, hydrogen bromide, hydrogen iodide, hydrogen cyanide, ammonia, carbon dioxide, carbon monoxide, acetylene, methyl-acetylene, propadiene, sulfur dioxide, mercaptans, carbonyl sulfide, carbon disulfide, ethane, propane, ethylene, propylene, phosgene, arsine, phosphine, and oxygen, and the background reference analyte comprises one or more gases selected from hydrocarbons fluoro-carbons, chioro-carbons, freons, water vapor, ammoma, carbon monoxide, carbon dioxide, nitrogen, oxygen, chlorine, hydrogen, methane, ethane, propane, butane, pentane, hexane, septane, octane, nonane, decane, ethylene, propylene, butene, acetylene, vinyl-chloride , acrylonitrile, and acetonitrile.

3. A method as in claim 1, wherein the target analyte is water vapor, the background reference analyte is methane, and the target wavelength and reference wavelength are chosen from groups consisting of approximately 1392.54 nm for the target wavelength and approximately 1392.36 nm, approximately 1392.41 nm, or approximately 1392.55 nm for the reference wavelength; approximately 1395.00 nm for the target wavelength and approximately 1395.03 nm or approximately 1394.99 nm for the reference wavelength; approximately 1854.03 nm for the target wavelength and approximately 1853.15 nm for the reference wavelength; approximately 1877.1 nm for the target wavelength and approximately 1877.05 nm for the reference wavelength; and approximately 1877.1 nm for the target wavelength and approximately 1876:99 nm for the reference wavelength.

4. A method as in claim 1, wherein the target analyte is carbon dioxide, the background reference analyte is ethane, the reference wavelength is approximately 2001.94 nm, and the target wavelength is chosen from the group consisting of approximately 2000.23 nm, approximately 2000.66 nm, approximately 2001.56 nm, approximately 2003.50 nm, approximately 2004.02 nm, and approximately 2004.55 nm.

5. A method as in claim 1, wherein the target analyte is carbon monoxide, the background reference analyte is methane, and the target wavelength and reference wavelength are chosen from groups consisting of approximately 2389.28 nm for the target wavelength and approximately 2389.32 nm for the reference wavelength, approximately 2381.00 nm for the target wavelength and approximately 2381.10 nm for the reference wavelength, approximately 2365.55 nm for the target wavelength and approximately 2365.48 nm for the reference wavelength, approximately 2663.13 nm for the target wavelength and approximately 2363.19 nm for the reference wavelength, approximately 360.75 nm for the target wavelength and approximately 2360.68 nm for the reference wavelength, approximately 2326.83 nm for the target wavelength and approximately 2326.78 nm or approximately 2326.92 nm for the reference wavelength, approximately 2323.63 nm for the target wavelength and approximately 2323.55 nm or approximately 2323.65 nm for the reference wavelength, and approximately 2313.71 nm for the target wavelength and approximately 2313.67 nm for the reference wavelength.

6. A method as in claim 1, further comprising:
collecting light absorption data at the target wavelength and the reference wavelength for one or more calibration gas samples having known concentrations of the target analyte and/or the background reference analyte; and
generating the background gas adjustment factor based on the light absorption data.

7. A method as in claim 1, wherein the light is provided by one or more light sources comprising one or more of a tunable diode laser, a tunable quantum cascade (QCL) serrucoriductor laser, a tunable horizontal cavity laser, a tunable vertical cavity surface emitting semiconductor laser (VCSEL), or a means for nonlinear frequency generation of tunable light.

8. A method as in claim 1, further comprising collecting the data quantifying the target absorption of light in the gas sample at the target wavelength and the reference absorption of light in the gas sample at the reference wavelength, the collecting comprising:
directing light from at least one light source through the gas sample, the light from the at least one light source comprising the target wavelength and the reference wavelength;
determining, using a photodetector upon which the light from the light source impinges after passing through the gas sample, the target absorption of light at the target wavelength in the gas sample and the reference absorption of light at the reference wavelength in the gas sample; and
passing the data quantifying the target absorption and the reference absorption from the photodetector to the one or more processors.

9. A method as in claim 8, wherein the at least one light source provides a light beam having a spectrally narrower emission bandwidth than the target analyte absorption and/or the reference analyte absorption.

10. A method as in claim 8, further comprising wavelength modulating the target wavelength and the reference wavelength to produce a harmonic output that is analyzed by a control unit or processor to calculate the background gas adjustment factor and the target analyte concentration.

11. A method as in claim 8, wherein the determining further comprises measuring a current and/or a voltage output from the a photodetector and wherein the calculating of the background gas adjustment factor comprises analyzing the measured current output by the one or more processors.

12. A method as in claim 1, further comprising collecting the data quantifying the target absorption of light in the gas sample at the target wavelength and the reference absorption of light in the gas sample at the reference wavelength, the collecting comprising:
   directing light from a first light source and a second light source through the gas sample, the light from the first light source comprising the target wavelength and the light from the second light source comprising the reference wavelength, wherein a path length of light absorption for the first and the second light sources is substantially identical;
   determining, using one or more photodetectors upon which the light from the first light source and the light from the second light source impinges after passing through the gas sample, the target absorption of light at the target wavelength in the gas sample and the reference absorption of light at the reference wavelength in the gas sample; and
   passing the data quantifying the target absorption and the reference absorption from the one or more photodetectors to the one or more processors.

13. A method as in claim 12, further comprising multiplexing light from the first and the second light sources into a single physical path through the gas sample.

14. A method as in claim 12, further comprising using different wavelength modulation frequencies for the first and second light sources.

15. A method as in claim 12, further comprising wavelength modulating the target wavelength and the reference wavelength to produce a harmonic output that is analyzed by a control unit or processor to calculate the background gas adjustment factor and the target analyte concentration.

16. A method as in claim 1, further comprising collecting the data quantifying the target absorption of light in the gas sample at the target wavelength and the reference absorption of light in the gas sample at the reference wavelength, the collecting comprising:
   directing light from a first laser source and a second laser source through the gas sample, the first and second laser sources providing first and second light beams with respective first and second wavelength scan ranges that include the first and the second wavelengths, wherein the first wavelength is provided in the first wavelength scan range and the second wavelength is provided in the second wavelength scan range;
   determining, using one or more photodetectors upon which the light from the first light source and the light from the second light source impinges after passing through the gas sample, the target absorption of light at the target wavelength in the gas sample and the reference absorption of light at the reference wavelength in the gas sample; and
   passing the data quantifying the target absorption and the reference absorption from the one or more photodetectors to the one or more processors.

17. A method as in claim 1, wherein the gas sample further comprises a second background reference analyte having a second interfering spectral feature at the target wavelength, the method further comprising:
   receiving, at one or more processors, second data quantifying a second reference absorption of light in the gas sample at a second reference wavelength, the second background reference analyte having a second resolvable spectral feature at the second reference wavelength and also a second interfering background spectral feature at the target wavelength;
   calculating, using at least one of the one or more processors, an inferred second background reference analyte absorption of the second background reference analyte at the target wavelength using a second background gas adjustment factor that relates measured light absorption at the second reference wavelength to light absorption by the second background reference analyte at the target wavelength; and
   calculating, using at least one of the one or more processors, the target analyte concentration in the gas sample by further adjusting the target absorption using the inferred second background reference analyte absorption to determine the calculated target analyte absorption at the target wavelength.

18. An apparatus comprising:
   a light source configured to provide a light beam comprising a target wavelength and a reference wavelength, the target wavelength selected to approximately coincide with a target analyte resolvable spectral feature in a gas sample, the reference wavelength selected to approximately coincide with a background reference analyte resolvable spectral feature in the gas sample, the background reference analyte also having an interfering spectral feature in the vicinity of the target wavelength;
   a photodetector configured to measure a target absorption at the target wavelength and a background absorption at the reference wavelength; and
   a control unit coupled to the photodetector and configured to calculate an inferred background reference analyte absorption at the target wavelength based on a measured absorption at the reference wavelength, the control unit using the inferred background reference analyte absorption to calculate the target analyte absorption at the target wavelength and thereby quantify the concentration of the target analyte in the gas sample.

19. An apparatus as in claim 18, further comprising a sample cell configured to contain the gas sample, the sample cell being positioned such that light from the light source passes through the gas sample.

20. An apparatus as in claim 18, wherein the control unit calculates the inferred background reference analyte absorption of the background reference analyte at the target wavelength using a background gas adjustment factor relating measured light absorption at the reference wavelength to light absorption by the background reference analyte at the target wavelength, the background gas adjustment factor being based on calibration data collected for one or more calibration samples containing the background reference analyte.

21. An apparatus as in claim 18, wherein the light source comprises a tunable diode laser, a tunable quantum cascade (QCL) semiconductor laser, a tunable horizontal cavity laser, a tunable vertical cavity surface emitting semiconductor laser (VCSEL), or a means for nonlinear frequency generation of tunable light.

22. An apparatus as in claim 18, wherein the control unit modulates a driving current for the light source and demodulates a direct current output from the photodetector to produce a harmonic output that is analyzed to calculate the background gas adjustment factor and the target analyte concentration.

23. An apparatus as in claim 18, wherein the target wavelength and reference wavelength are chosen from groups consisting of approximately 1392.54 nm for the target wavelength, and approximately 1392.36 nm, approximately 1392.41 nm, or approximately 1392.55 nm for the reference wavelength; approximately 1395.00 nm for the target wavelength and approximately 1395.03 nm or approximately 1394.99 nm for the reference wavelength; approximately 1854.03 nm for the target wavelength and approximately 1853.15 nm for the reference wavelength; approximately 1877.1 nm for the target wavelength and approximately 1877.05 nm for the reference wavelength; and approximately 1877.1 nm for the target wavelength and approximately 1876.99 nm for the reference wavelength.

24. An apparatus as in claim 18, wherein the target wavelength and reference wavelength are chosen from groups consisting of approximately 2000.23 nm, approximately 2000.66 nm, approximately 2001.56 nm, approximately 2003.50 nm, approximately 2004.02 nm, or approximately 2004.55 nm for the target wavelength and approximately 2001.94 nm for the reference wavelength; approximately 2389.28 nm for the target wavelength and approximately 2389.32 nm for the reference wavelength; approximately 2381.00 nm for the target wavelength and approximately 2381.10 nm for the reference wavelength; approximately 2365.55 nm for the target wavelength and approximately 2365.48 nm for the reference wavelength; approximately 2663.13 nm for the target wavelength and approximately 2363.19 nm for the reference wavelength; approximately 2360.75 nm for the target wavelength and approximately 2360.68 nm for the reference wavelength; approximately 2326.83 nm for the target wavelength and approximately 2326.78 nm or approximately 2326.92 nm for the reference wavelength; approximately 2323.63 nm for the target wavelength and approximately 2323.55 nm or approximately 2323.65 nm for the reference wavelength; and approximately 2313.71 nm for the target wavelength and approximately 2313.67 nm for the reference wavelength.

25. An apparatus as in claim 18, wherein the light source comprises a first laser that provides a first beam comprising the target wavelength and a second laser that provides a second beam comprising the reference wavelength.

26. An apparatus comprising:
a light source configured to provide a light beam comprising a light at a target wavelength of approximately 1877.1 nm and a reference wavelength of approximately 1877.05 nm, a photodetector configured to measure a target absorption for water vapor at the target wavelength and a background absorption for methane at the reference wavelength; and
a control unit coupled to the photodetector and configured to calculate an inferred background reference analyte absorption for methane at the target wavelength based on a measured absorption at the reference wavelength, the control unit using the inferred background analyte absorption for methane to calculate the target analyte absorption at the target wavelength and thereby quantify the concentration of the water vapor in the gas sample.

27. A method comprising:
passing light from one or more laser light sources providing at least a first wavelength and a second wavelength through a gas stream that comprises a target analyte and a background compound, the target analyte having a resolvable target spectral feature at the first wavelength, the background compound having a first background spectral feature at the first wavelength and a second background spectral feature at the second wavelength, the gas stream comprising a background compound concentration and a target analyte concentration, at least the background compound concentration being temporally variable;
quantifying a first total absorption of the light at the first wavelength and a second total absorption of the light in the gas sample at the second wavelength;
inferring a background contribution of the first total absorption that is due to the first background spectral feature, the inferring comprising assuming that the second total absorption is due to the second background spectral feature of the background compound and converting the second total absorption into the background contribution based on second calibration data collected at the first wavelength and the second wavelength for one or more second standard samples having known second concentrations of the background compound;
calculating a target analyte contribution to the first total absorption by correcting the first total absorption with the background contribution; and
determining the target analyte concentration in the gas sample based on the target analyte contribution to the first total absorption and first calibration data collected at the first wavelength for one or more first standard samples having known first concentrations of the target analyte.

* * * * *